United States Patent
Mashiach

(10) Patent No.: US 9,526,906 B2
(45) Date of Patent: Dec. 27, 2016

(54) EXTERNAL RESONANCE MATCHING BETWEEN AN IMPLANTED DEVICE AND AN EXTERNAL DEVICE

(71) Applicant: Adi Mashiach, Tel Aviv (IL)

(72) Inventor: Adi Mashiach, Tel Aviv (IL)

(73) Assignee: NYXOAH SA, Mont-st-Guibert (BE)

( * ) Notice: Subject to any disclaimer, the term of this patent is extended or adjusted under 35 U.S.C. 154(b) by 0 days.

(21) Appl. No.: 13/952,063

(22) Filed: Jul. 26, 2013

(65) Prior Publication Data
US 2014/0031903 A1    Jan. 30, 2014

Related U.S. Application Data

(60) Provisional application No. 61/676,327, filed on Jul. 26, 2012.

(51) Int. Cl.
*A61N 1/372* (2006.01)
*A61N 1/378* (2006.01)
(Continued)

(52) U.S. Cl.
CPC ......... *A61N 1/3787* (2013.01); *A61B 17/0482* (2013.01); *A61N 1/0526* (2013.01);
(Continued)

(58) Field of Classification Search
CPC .. A61N 1/3601; A61N 1/3605; A61N 1/3787; A61N 1/37205; A61N 1/08; A61N 1/3606; A61N 1/3611; A61N 1/36125; A61N 1/37229; A61N 1/375
(Continued)

(56) References Cited

U.S. PATENT DOCUMENTS 5,463,285 A * 10/1995 El-Hamamsy ................ 315/248
6,477,425 B1   11/2002 Nowick et al.
(Continued)

FOREIGN PATENT DOCUMENTS

EP        2 468 358       6/2012
WO    WO 2007/118194    10/2007

OTHER PUBLICATIONS

International Search Report and Written Opinion, PCT/IB13/02155, Mar. 18, 2014, 15 pages.

*Primary Examiner* — Christopher D Koharski
*Assistant Examiner* — Pamela M Bays
(74) *Attorney, Agent, or Firm* — Finnegan, Henderson, Farabow, Garrett & Dunner LLP

(57) ABSTRACT

Some embodiments of the disclosure may include a device for wirelessly powering an implant unit in a body of a subject from a location outside of the body of the subject, wherein the implant unit includes a secondary antenna for wirelessly receiving energy. The device may include a primary antenna configured to be located external to the body of the subject, a circuit electrically connected to the primary antenna, and at least one processor electrically connected to the primary antenna and the circuit. The at least one processor may determine a resonant frequency mismatch between a first resonant frequency associated with the primary antenna and a second resonant frequency associated with the secondary antenna associated with the implant unit; and apply an adjustment to at least one component of the circuit to cause a change in the first resonant frequency associated with the primary antenna and a reduction in the resonant frequency mismatch.

19 Claims, 12 Drawing Sheets

(51) Int. Cl.
    *A61N 1/05*         (2006.01)
    *A61B 17/04*       (2006.01)
    *A61N 1/36*         (2006.01)
    *H04B 5/00*         (2006.01)
    *H02J 7/02*         (2016.01)
    *A61N 1/375*       (2006.01)

(52) U.S. Cl.
    CPC ......... *A61N 1/0548* (2013.01); *A61N 1/0558* (2013.01); *A61N 1/3601* (2013.01); *A61N 1/36003* (2013.01); *A61N 1/3605* (2013.01); *A61N 1/3606* (2013.01); *A61N 1/3611* (2013.01); *A61N 1/36071* (2013.01); *A61N 1/36075* (2013.01); *A61N 1/36117* (2013.01); *A61N 1/36125* (2013.01); *A61N 1/36132* (2013.01); *A61N 1/36189* (2013.01); *A61N 1/375* (2013.01); *A61N 1/37229* (2013.01); *H02J 7/025* (2013.01); *H04B 5/0037* (2013.01); *H04B 5/0031* (2013.01); *H04B 5/0081* (2013.01); *H04B 5/0093* (2013.01); *Y10T 29/49018* (2015.01)

(58) Field of Classification Search
    USPC .................................. 607/32, 33, 42, 60, 61
    See application file for complete search history.

(56) References Cited

U.S. PATENT DOCUMENTS

| | | |
|---|---|---|
| 7,015,769 B2 | 3/2006 | Schulman et al. |
| 7,096,068 B2 | 8/2006 | Mass et al. |
| 7,209,792 B1 | 4/2007 | Parramon et al. |
| 7,225,032 B2 | 5/2007 | Schmeling et al. |
| 7,286,880 B2 | 10/2007 | Olson et al. |
| 7,467,014 B2 | 12/2008 | Fuller et al. |
| 7,648,499 B2 | 1/2010 | Orszulak et al. |
| 7,756,587 B2 | 7/2010 | Penner et al. |
| 8,140,167 B2 | 3/2012 | Donders et al. |
| 8,140,168 B2 | 3/2012 | Olson et al. |
| 8,195,305 B2 | 6/2012 | Nghiem et al. |
| 8,260,412 B2 | 9/2012 | Krause et al. |
| 8,335,569 B2 | 12/2012 | Aghassian |
| 2005/0075697 A1 | 4/2005 | Olson et al. |
| 2005/0075700 A1* | 4/2005 | Schommer et al. ............ 607/61 |
| 2005/0119716 A1 | 6/2005 | McClure et al. |
| 2006/0142822 A1 | 6/2006 | Tulgar |
| 2006/0192628 A1 | 8/2006 | Schulman et al. |
| 2007/0004994 A1* | 1/2007 | Sherman ........................ 602/26 |
| 2007/0167997 A1* | 7/2007 | Forsberg et al. ............... 607/61 |
| 2008/0021506 A1* | 1/2008 | Grocela ............................ 607/9 |
| 2008/0319285 A1 | 12/2008 | Hancock |
| 2010/0076524 A1* | 3/2010 | Forsberg et al. ............... 607/61 |
| 2010/0241040 A1 | 9/2010 | Sherman |
| 2011/0022123 A1 | 1/2011 | Stancer et al. |
| 2012/0026009 A1 | 2/2012 | Zhao et al. |
| 2012/0095531 A1 | 4/2012 | Derbas et al. |
| 2012/0153735 A1 | 6/2012 | Karalis et al. |
| 2012/0235502 A1 | 9/2012 | Kesler et al. |
| 2012/0235503 A1 | 9/2012 | Kesler et al. |
| 2012/0235633 A1 | 9/2012 | Kesler et al. |
| 2012/0262108 A1* | 10/2012 | Olson .................. A61N 1/3787 320/108 |
| 2012/0283800 A1 | 11/2012 | Perryman et al. |
| 2012/0286582 A1 | 11/2012 | Kim et al. |

\* cited by examiner

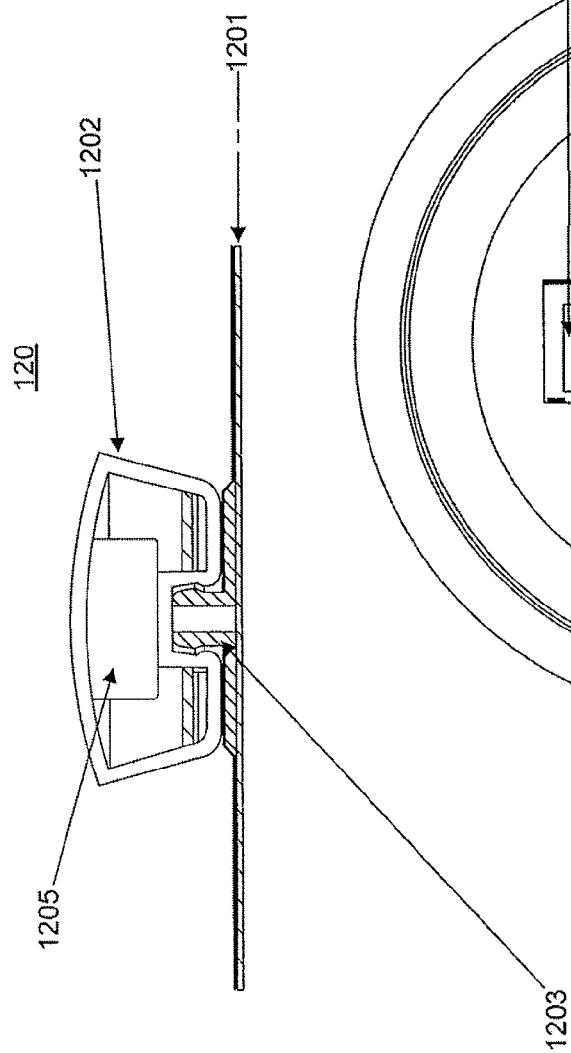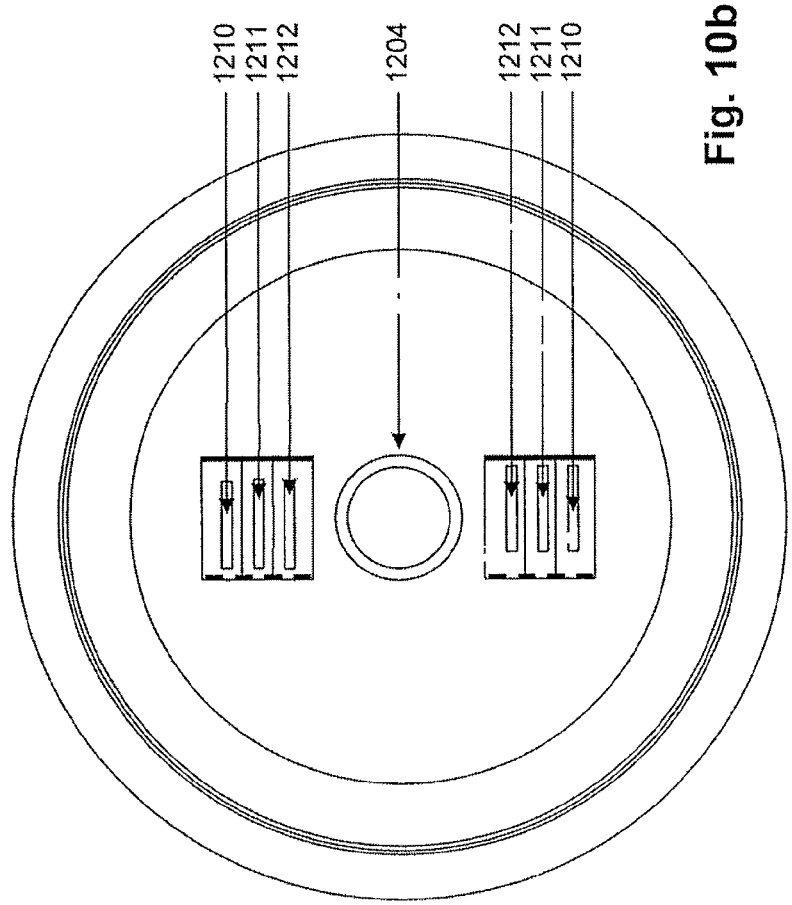

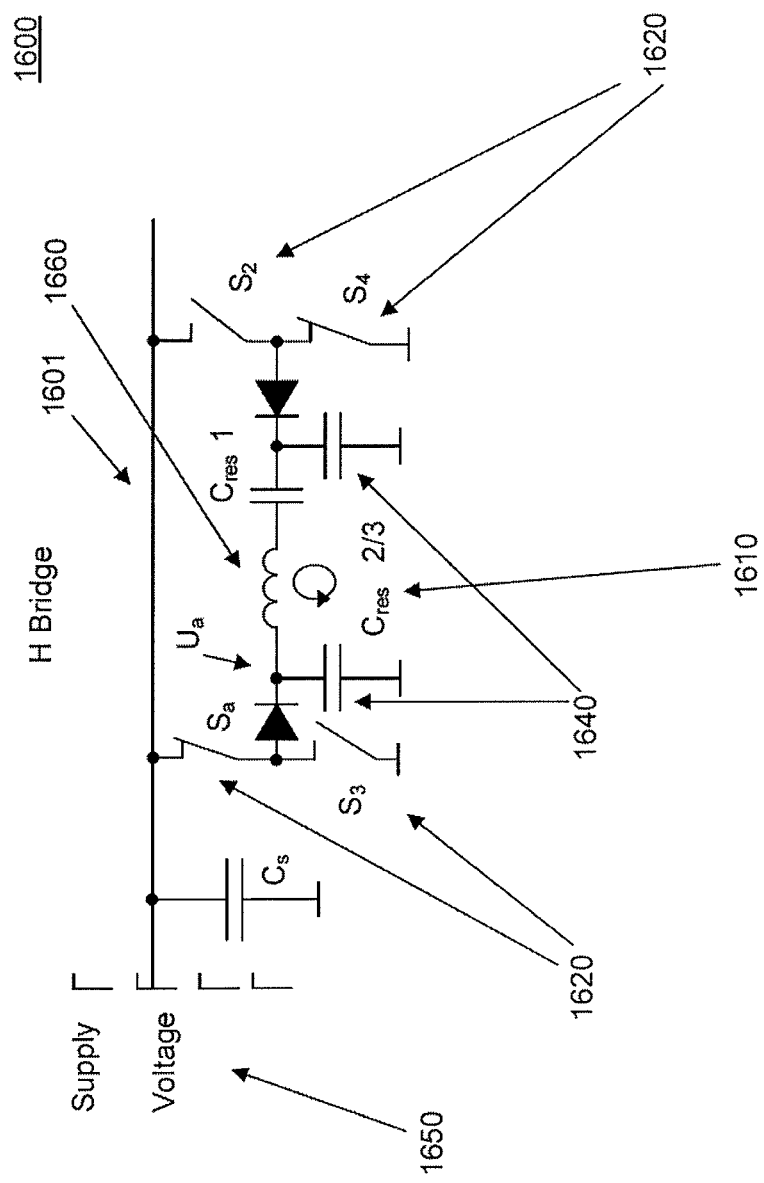

EXTERNAL RESONANCE MATCHING BETWEEN AN IMPLANTED DEVICE AND AN EXTERNAL DEVICE

CROSS-REFERENCES TO RELATED APPLICATIONS

The present application claims the benefit of a U.S. Provisional Patent Application No. 61/676,327, filed on Jul. 26, 2012, the disclosure of which is incorporated herein by reference.

TECHNICAL FIELD

Embodiments of the present disclosure generally relate to devices and methods for modulating a nerve. More particularly, embodiments of the present disclosure relate to devices and methods for powering an implant unit.

BACKGROUND

Neural modulation presents the opportunity to treat many physiological conditions and disorders by interacting with the body's own natural neural processes. Neural modulation includes inhibition (e.g., blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is obstructive sleep apnea (OSA). OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to patients with hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g., through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit. But the embodiments of the invention described hereafter are not necessarily limited to treating only the above-described conditions.

SUMMARY

Some embodiments of the disclosure may include a device for wirelessly powering an implant unit in a body of a subject from a location outside of the body of the subject, wherein the implant unit includes a secondary antenna for wirelessly receiving energy. The device may include a primary antenna configured to be located external to the body of the subject, a circuit electrically connected to the primary antenna, and at least one processor electrically connected to the primary antenna and the circuit. The at least one processor may determine a resonant frequency mismatch between a first resonant frequency associated with the primary antenna and a second resonant frequency associated with the secondary antenna associated with the implant unit; and apply an adjustment to at least one component of the circuit to cause a change in the first resonant frequency associated with the primary antenna and a reduction in the resonant frequency mismatch.

In some other embodiments, the device may include a primary antenna configured to be located external to a subject, a circuit electrically connected to the primary antenna and associated with a plurality of selectable capacitance values. The device may also include at least one processor configured to determine a transmission efficiency value between the primary antenna and the secondary antenna for each of a plurality of frequencies; and select a capacitance value to be included in the circuit, from among the plurality of selectable capacitance values, based on the determined transmission efficiencies.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIG. 10A is a diagrammatic side view of an external unit according to an exemplary embodiment of the present disclosure.

FIG. 10B is a diagrammatic top view of the external unit according to the exemplary embodiment of FIG. 10A.

FIG. 11 is circuit diagram depicting a self-resonant transmitter employing a modified class D amplifier.

DESCRIPTION OF EXEMPLARY EMBODIMENTS

Figure 1:
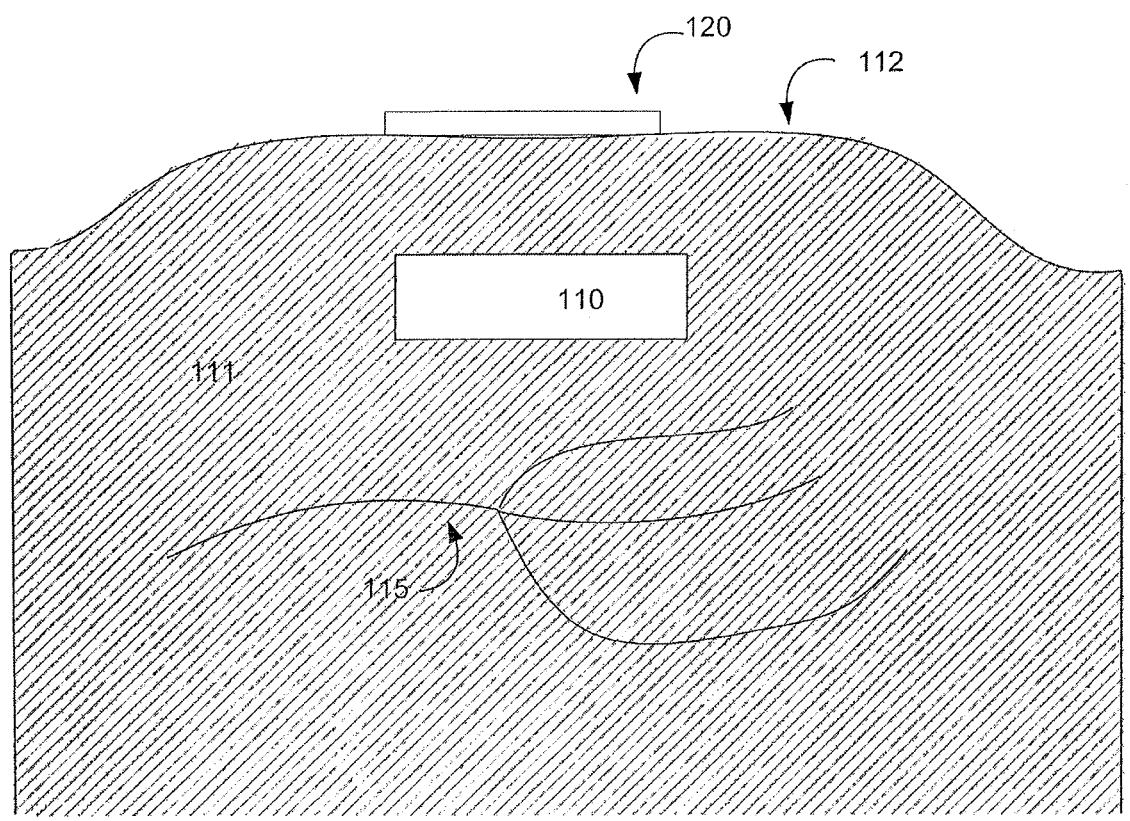
FIG. 1 is a diagrammatic illustration of an implanted unit and external unit, according to an exemplary embodiment of the present disclosure.

Reference will now be made in detail to exemplary embodiments of the present disclosure, examples of which are illustrated in the accompanying drawings. Wherever possible, the same reference numbers will be used throughout the drawings to refer to the same or like parts.

Some embodiments of the present disclosure relate to a device (also referred to as an external unit) having a primary antenna wirelessly powering an implantable device (also referred to as an implant unit) having a secondary antenna. When the two antennas are in resonant frequency match, the efficiency of energy transfer between the external unit and the implant unit may be higher than circumstances in which a resonant frequency associated with the primary antenna of the external unit does not match a resonant frequency associated with the secondary antenna of the implant unit. In some cases, however, the resonant frequency associated with the secondary antenna on the implant unit may change over time for a variety of reasons, including, for example, as a result of effects associated with implantation in the subject's body. The present disclosure describes embodiments configured to change or reduce a frequency mismatch between a resonant frequency associated with the secondary antenna of the implant unit and a resonant frequency associated with the primary antenna of the external unit.

The implantable device may be employed, for example, to modulate at least one nerve in the subject's body. Nerve modulation, or neural modulation, includes inhibition (e.g., blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may include providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with OSA, for example, a primary target response of nerve stimulation may include contraction of a tongue muscle (e.g., including a genioglossus muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/ portion of a body where nerve modulation may be desired. That is, in addition to use in patients with OSA, migraine headaches, or hypertension, embodiments of the present disclosure may be used in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

FIG. 1 illustrates an implant unit and external unit, according to an exemplary embodiment of the present disclosure. An implant unit 110, may be configured for implantation in a subject (e.g., a patient), in a location that permits it to modulate a nerve 115. Implant unit 110 may be located in a subject such that intervening tissue 111 exists between implant unit 110 and nerve 115. Intervening tissue may include muscle tissue, connective tissue, organ tissue, or any other type of biological tissue. Thus, location of implant unit 110 does not require contact with nerve 115 for effective neuromodulation. Implant unit 110 may also be located directly adjacent to nerve 115, such that no intervening tissue 111 exists. In further embodiments, the implant unit may be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e., the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

In further embodiments, the implant unit may be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e., the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Figure 2:
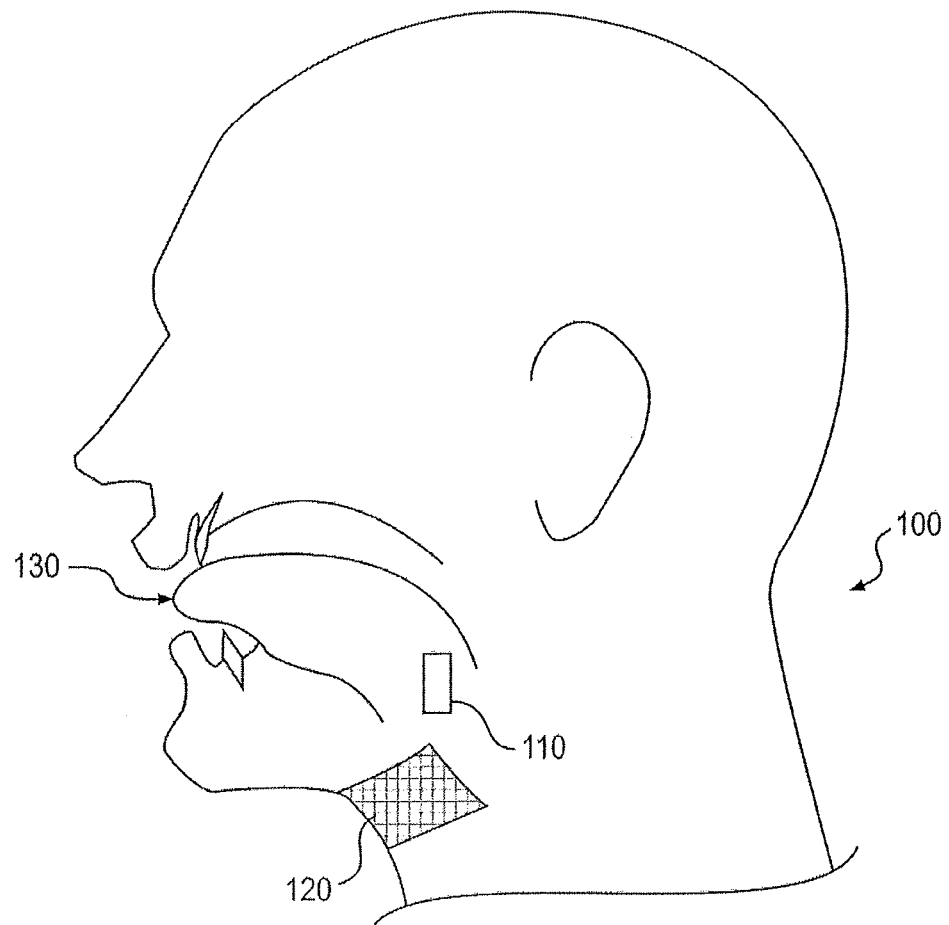
FIG. 2 is a partially cross-sectioned side view of a patient with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to patient 100. FIG. 2 illustrates that in patient 100 with OSA, external unit 120 may be configured for placement underneath the patient's chin and/or on the front of patient's neck. The suitability of placement locations may be determined by communication between external unit 120 and implant unit 110, discussed in greater detail below. In alternate embodiments, for the treatment of conditions other than OSA, the external unit may be configured to be affixed anywhere suitable on a patient. Such as: on the back of a patient's neck for communication with a migraine treatment implant unit, on the outer portion of a patient's abdomen for communication with a stomach modulating implant unit, on a patient's back for communication with a renal artery modulating implant unit, and/or on any other suitable external location on a patient's skin, depending on the requirements of a particular application.

In some embodiments external unit 120 may be configured for location external to a patient, either directly contacting, or close to the skin 112 of the patient. Accordingly, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
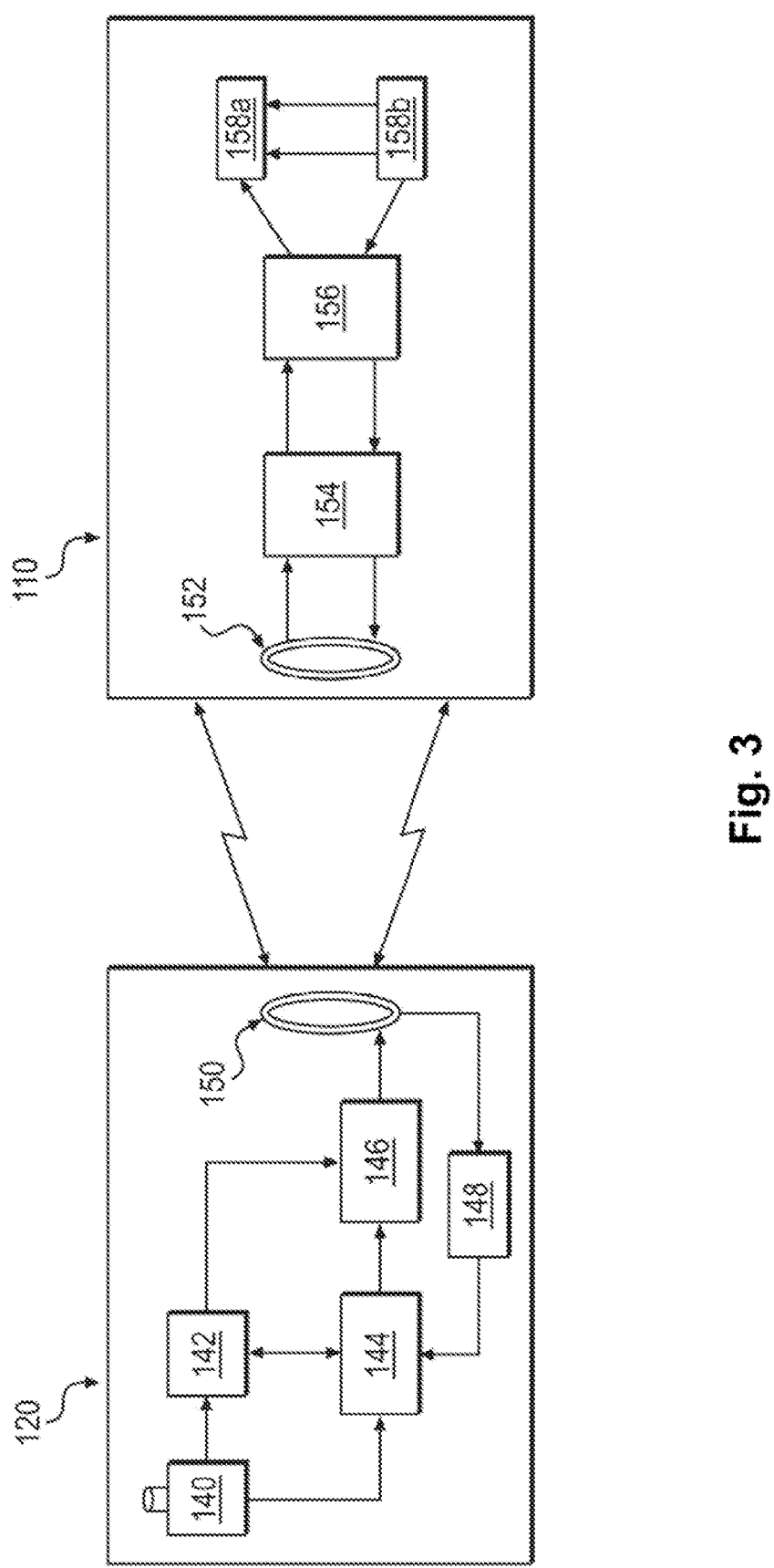
FIG. 3 is a diagrammatic block chart illustrating a system including an implant unit and an external unit, according to an exemplary embodiment of the present disclosure.

FIG. 3 is a diagrammatic representation of an exemplary device (e.g., external unit 120) and exemplary implantable unit (e.g., implant unit 110). In one embodiment, implant unit 110 may comprise a carrier (e.g., flexible carrier 161 illustrated in FIG. 4), an implantable circuit (e.g., circuit 180 illustrated in FIG. 6), an antenna (e.g., secondary antenna 152), and at least one component for receiving energy from the implantable circuit (e.g., implant electrodes 158a, 158b). Prior to implantation in the subject's body, the implantable circuit and the secondary antenna provide a certain resonant frequency. When implanted in the body of the subject, however, this resonant frequency may change due, for example, to various effects associated with locating the implant unit into the body of the subject. In some embodiments, the changes to the resonant frequency associated with the implant unit after implantation may be known, predictable, or predicted, etc. To account for this change in resonant frequency (or resonant frequency drift), the implant unit may be manufactured to have a resonant frequency associated with the antenna and implantable circuit that is mismatched from a resonant frequency of an external circuit (e.g., circuit 170) configured to communicate with the implantable circuit of the implant unit. This resonant frequency mismatch may be eliminated after the implant unit is placed in the body of the subject and changes in the resonant frequency associated with the implant unit occur.

The implant unit may be formed from any materials suitable for implantation into the body of a patient. In some embodiments, the implant unit may include a carrier formed of a flexible, biocompatible material to provide a flexible carrier 161. In some embodiments, the flexible carrier may function as a substrate for the implant unit upon which various components of the implant unit are formed, placed, disposed, etc. Materials that may be used in forming the flexible carrier include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

The implant unit and the external unit each may include a circuit, including at least one wire, electrical component, resistor, inductor, and/or capacitor, etc.) electrically connected either directly or indirectly to their respective antennas. In some embodiments, the circuit for the implant unit may include, for example, capacitor 151, diode 156, and a harmonics modifier circuit 154, which may be used to non-linearly alter the harmonics generated in the circuitry. The circuit of the implantable unit may include or connect with other electrical components including, for example, electrodes, switches, transducers, sensors, detectors, antennas, diodes, etc. One example of a circuit that may be included on implant unit 110 is circuit 180 depicted in FIG. 6.

In some embodiments, the circuit may include at least one capacitor (e.g., two capacitors, eight capacitors) configured to be selectively included and selectively excluded from the electrical circuit. For example, switches may be included in the circuit and associated with the capacitors in order to selectively include or exclude any of a plurality of capacitors from the electrical circuit. The term "capacitor" refers to any device configured for storing an electric charge. In some cases, the circuits of the external unit and implant unit may comprise a plurality of capacitors (e.g., four capacitors, six capacitors, or ten capacitors) selectable by a processor, for example. In other cases the circuits of external unit 110 and implant unit 120 may include at least one trimming capacitor having an adjustable capacitance value, or at least one frequency-dependent capacitor. In such embodiments, the trimming capacitor may be used to provide a plurality of different capacitance values. The plurality of capacitance values may be discrete. Alternatively or additionally, the capacitance may be variable over a continuous range and may be selected at any value within the range.

As shown in FIG. 3, both external unit 120 and implant unit 110 may include an antenna. The antenna of the external unit (e.g., primary antenna 150) and the antenna of the implant unit (e.g., secondary antenna 152) may include any conductive structure that may be configured to send, transmit, emit, and/or receive electromagnetic signals. The antenna may have any suitable size, shape, and/or configuration. In some embodiments, the number of antennas, their size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. Exemplary antennas may include, but are not limited to, a long-wire antenna, a patch antenna, a helical antenna, a coil antenna, a slow wave antenna, a monopole antenna, a dipole antenna, spiral, oval, rectangular, spiderweb, etc.

In some embodiments the implantable unit (e.g., implant unit 110) may include an antenna (e.g., secondary antenna 152) mounted onto or integrated with flexible carrier 161. The antenna may be arranged on the carrier and configured to wirelessly receive energy from a location external to the subject's body and to provide at least a portion of the energy to the implantable circuit. For example, secondary antenna 152 may include a coil antenna having a circular shape (see also FIG. 4 and FIG. 5) or oval shape. Such a coil antenna may include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g., 4, 15, 20, 30, or 50. A coil antenna suitable for use as secondary antenna 152 may have a wire diameter between about 0.001 mm and 1 mm. These antenna parameters are exemplary only, and may be adjusted above or below the ranges given to achieve suitable results.

Figure 4:
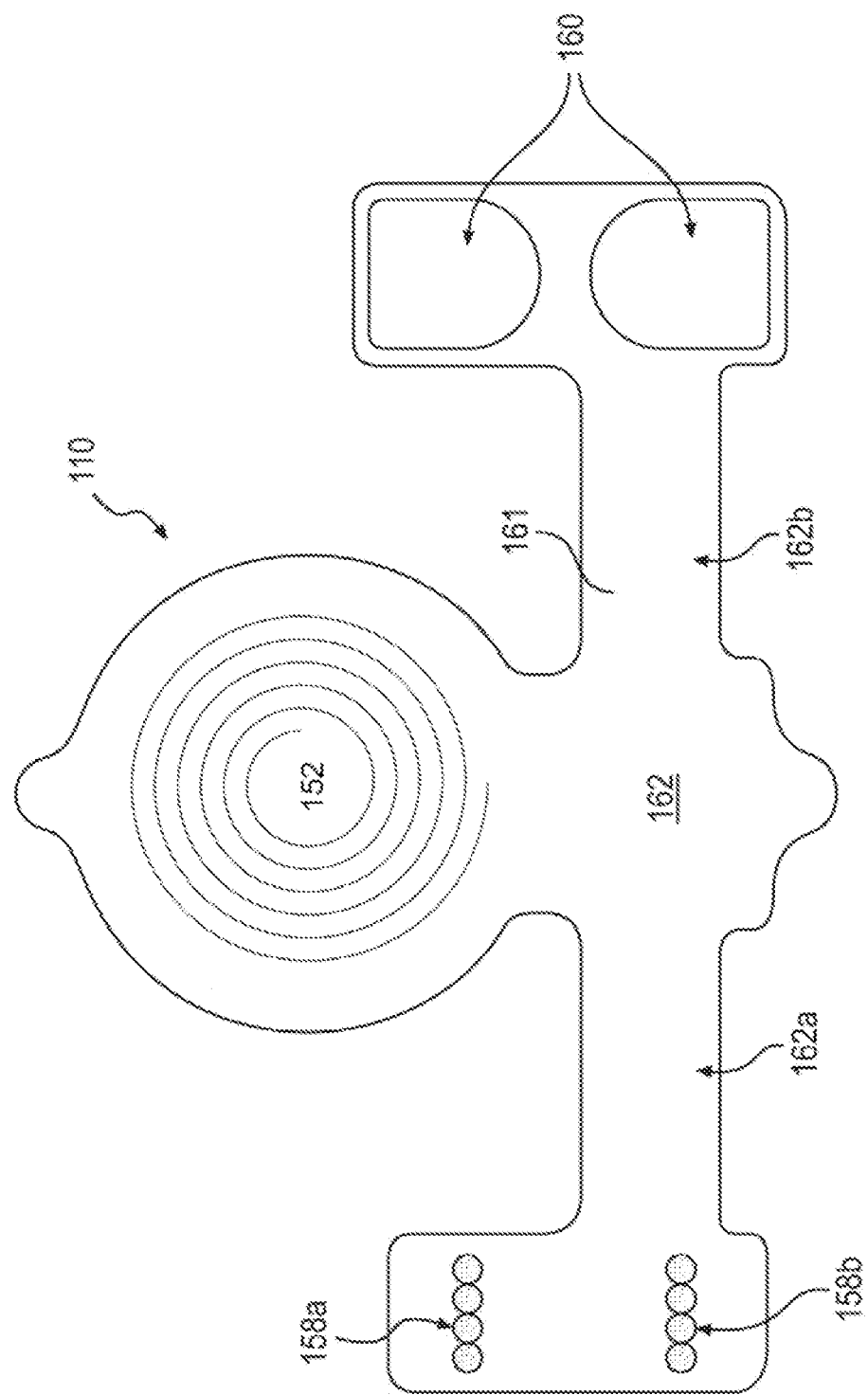
FIG. 4 is a diagrammatic top view of an implant unit, according to an exemplary embodiment of the present disclosure.

The implantable unit (e.g., implant unit 110) may additionally include at least one component associated with the carrier for receiving energy from the implantable circuit. In some embodiments the at least one component may include a pair of modulation electrodes (e.g., implant electrodes 158a and 158b). The modulation electrodes may include any suitable shape and/or orientation on the implant unit so long as the electrodes may generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes located at a plurality of locations, for example on an end of both a first extension 162a and a second extension 162b of elongate arm 162, as illustrated, for example, in FIG. 5. Implant electrodes may have a thickness between about 200 nanometers and 1 millimeter. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

In other embodiments the at least one component includes a lamp. The term "lamp" refers to any device configured to emit electromagnetic radiation. For example, infrared radiation, visible light radiation, etc. The lamp may use a light emitting diode (LED) as an implantable source of optical stimulation for gene therapy.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. Additionally, or alternatively, implant unit 110 may include surgical mesh 1050 or other perforatable material, described in greater detail below with respect to FIG. 10. In some embodiments, implant unit may appear substantially as illustrated in FIG. 4. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body.

Figure 5:
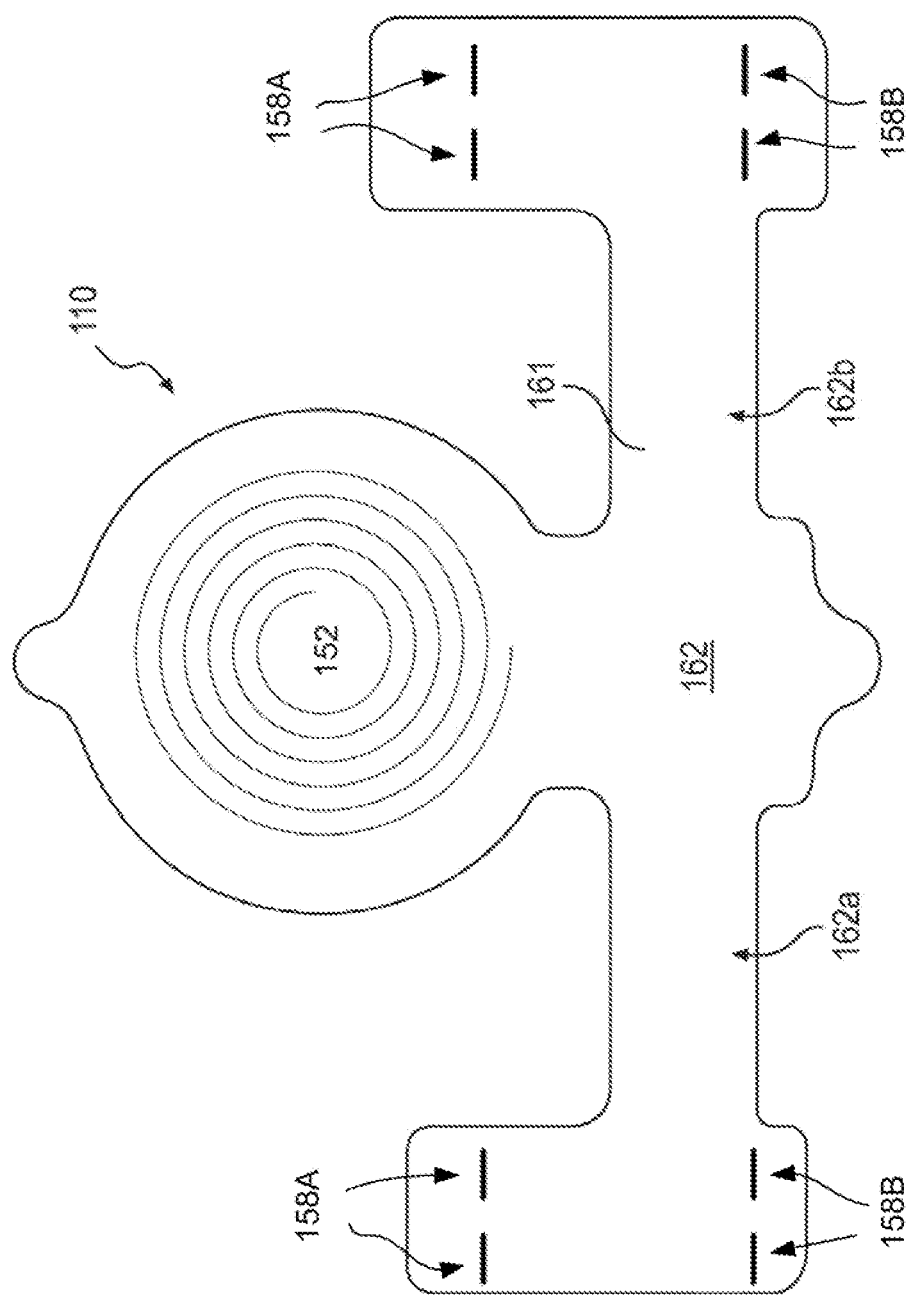
FIG. 5 is a diagrammatic top view of an alternate embodiment of an implant unit.

As illustrated in FIG. 4, secondary antenna 152 and electrodes 158a, 158b may be mounted on or integrated with flexible carrier 161. Various circuit components and connecting wires (discussed further below) may be used to connect secondary antenna with implant electrodes 158a and 158b. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers FIG. 5 is a perspective view of an alternate embodiment of an implant unit 110, according to an exemplary embodiment of the present disclosure. As illustrated in FIG. 5, implant unit 110 may include a plurality of electrodes, located, for example, at the ends of first extension 162a and second extension 162b. FIG. 5 illustrates an embodiment wherein implant electrodes 158a and 158b include short line electrodes.

As mentioned above, FIG. 3 is a diagrammatic representation of an exemplary device (e.g., external unit 120) and exemplary implantable unit (e.g., implant unit 110). In one embodiment, external unit 120 may comprise a primary antenna (e.g., primary antenna 150), a circuit (e.g., circuit 170 illustrated in FIG. 6), and at least one processor (e.g., processor 144). The at least one processor may determine a resonant frequency mismatch between the primary antenna and an antenna associated with the implant unit (e.g., secondary antenna 152). The at least one processor may also cause a change in a resonant frequency of the primary antenna to reduce the resonant frequency mismatch.

In some embodiments the antenna of the external unit (e.g., primary antenna 150) may be a coil antenna having a diameter of between about 1 cm to 10 cm, and may be circular or oval shaped. For example, primary antenna 150 may be a coil antenna having a diameter between 5 cm and 7 cm, and any number of windings, e.g., 4, 8, 12, or more. A coil antenna suitable for use as antenna 150 may have a wire diameter between about 0.01 mm and 2 mm. These antenna parameters are exemplary only, and may be adjusted above or below the ranges given to achieve suitable results. Primary antenna 150 may be configured as part of external unit 120 and may be coupled either directly or indirectly to various components in external unit 120. For example, as shown in FIG. 3, primary antenna 150 may have an electric connection to amplifier 146.

In some embodiments, the external unit may include a circuit electrically connected to the primary antenna. The circuit may include processor 144, power source 140, signal source 142, amplifier 146, at least one capacitor 141, and feedback circuit 148. The circuit of the external unit may include other electrical components, for example, switches, transducers, sensors, detectors, antennas, diodes, etc. For example, the external unit may include an electrical circuit 170 similar to the circuit elements illustrated in FIG. 6.

In some embodiments, the external unit may comprise at least one processor 144. In some embodiments, processor 144 may be located within the housing of external unit 120. In alternative embodiments, the at least one processor may be configured for wired or wireless communication with the external unit from a location remote from the housing. The term "processor" as used herein refers to a device that includes any suitable logic or computational components configured according to the requirements of a particular application. In some embodiments, the processor may include any physical device having an electric circuit that performs a logic operation on input or inputs. For example, processor 144 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by the controller may, for example, be preloaded into a memory unit integrated with or embedded into the controller or may be stored in a separate memory unit, such as a Random Access Memory (RAM), a Read-Only Memory (ROM), a hard disk, an optical disk, a magnetic medium, a flash memory, other permanent, fixed, or volatile memory, or any other mechanism capable of storing instructions for the controller. In case more than one controller or processor is employed, all may be of similar construction, or they may be of differing constructions electrically connected or disconnected from each other. They may be separate circuits or integrated in a single circuit. When more than one controller or processor is used, they may operate independently or collaboratively. They may be coupled electrically, magnetically, optically, acoustically, mechanically or by other means permitting them to interact. In some embodiments, the at least one processor may be associated with a memory.

In some embodiments, illustrated in FIG. 3, the external unit 120 may include a power source 140. Power source 140 may be permanently or removably coupled to a location within external unit 120. The power source may further include any suitable source of power configured to be in electrical communication with the processor. For example, power source 140 may include a battery, such as a paper battery, thin film battery, or other type of battery. In some embodiments, power source 140 may include a substantially flat, flexible battery.

The power source may power various components within the external unit. For example, power source 140 may provide power to processor 144 and signal source 142. Signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may generate alternating current (AC) signals and/or direct current (DC) signals. In one embodiment, signal source 142 may generate an AC signal for transmission to one or more other components. Signal source 142 may generate a signal of any suitable frequency. In some embodiments, signal source 142 may generate a signal having a frequency of from about 6.5 MHz to about 13.6 MHz. In additional embodiments, signal source 142 may generate a signal having a frequency of from about 7.4 to about 8.8 MHz. In further embodiments, signal source 142 may generate a signal having a frequency as low as 90 kHz or as high as 28 MHz.

Signal source 142 may be electrically connected, either directly or indirectly, to amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated with one or more aspects of a signal. The amplifier may further output the amplified signals to one or more components within external unit 120.

Signal source 142 may also be electrically connected, either directly or indirectly, to at least one capacitor 141. At least one capacitor 141 may include any suitable device configured for storing an electric charge. In some embodiments, external unit 120 may include a single capacitor associated, and this capacitor may be associated with a processor. Processor 144 may be able to select at least two different values of capacitance offered by the capacitor. For example, processor may be configured to apply the capacitance to a circuit associated with a primary antenna in the external unit. Changing the capacitance in this way may change the resonant frequency associated with the primary antenna of the external unit. The capacitor may be one having a fixed capacitance. In some embodiments, the capacitor may be trimmable such that multiple capacitance values may be provided by the single capacitor.

In other embodiments, external unit 120 may include a plurality of capacitors that may be selectively included or excluded from circuitry associated with the primary antenna. For example, external unit 120 may include a bank of capacitors (e.g., 4, 6, or more). Processor 144 may be configured to selectively include or exclude any of the plurality capacitors into the circuitry associated with the primary antenna in order to change the resonant frequency associated with the primary antenna. In one example, a bank of six capacitors may permit the processor to select a capacitance value from 64 (i.e., $2^6$) different possible values.

FIGS. 10A and 10B illustrate an example of the external unit according to some embodiments. The example illustrates features that may be found in any combination in other embodiments. FIG. 10A illustrates a side view of external unit 120, depicting carrier 1201 and electronics housing 1202.

Carrier 1201 may include a skin patch configured for adherence to the skin of a subject, for example through adhesives of mechanical means. Carrier 1201 may be flexible or rigid, or may have flexible portions and rigid portions. Carrier 1201 may include a connector 1203 configured for selectively or removably connecting carrier 1201 to electronics housing 1202. Connector 1203 may extend or protrude from carrier 1201. Connector 1203 may be received by a recess 1204 of electronics housing 1202. Connector 1203 may be configured as a connector providing a selective connection to electronics housing 1204 without the substantial use of a concave feature. Connector 1203 may include, for example a peg, or another connective element extending from carrier 1201. Connector 1203 may further include a magnetic connection, a velcro connection, and/or a snap dome connection. Connector 1203 may also include a locating feature, configured to locate electronics housing 1202 at a specific height, axial location, and/or axial orientation with respect to carrier 1201. A locating feature of connector 1203 may further include pegs, rings, boxes, ellipses, bumps, etc. Connector 1203 may be centered on carrier 1201, may be offset from the center by a predetermined amount, or may be provided at any other suitable location of carrier 1201. Multiple connectors 1203 may be provided on carrier 1201. Connector 1203 may be configured such that removal from electronics housing 1202 causes breakage of connector 1203. Such a feature may be desirable to prevent re-use of carrier 1201, which may lose some efficacy through continued use.

In some embodiments the external unit may include a housing. The housing may include any suitable container configured for retaining components. While only one embodiment of housing is illustrated schematically in FIGS. 10A and 10B, other embodiments of housing may include any suitable size and/or shape and may be rigid or flexible. External unit 120 may include one or more of patches, buttons, or other receptacles having varying shapes and dimensions constructed of any suitable material. In one embodiment, external unit 120 may include a flexible material enabling external unit to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

Electronics housing 1202 may include electronics portion 1205, which may be arranged inside electronics housing 1202 in any manner that is suitable. Electronics portion 1205 may include various components, further discussed below, of external unit 120. For example, electronics portion 1205 may include any combination of at least one processor 144 associated with external unit 120, a power source 140, such as a battery, a primary antenna 152, and an circuit 170. Electronics portion 1205 may also include any other component described herein as associated with external unit 120. Additional components may also be recognized by those of skill in the art.

Electronics housing 1202 may include a recess 1204 configured to receive connector 1203. Electronics housing 1202 may include at least one electrical connector 1210, 1211, 1212. Electrical connectors 1210, 1211, 1212 may be arranged with pairs of electrical contacts, as shown in FIG. 10B, or with any other number of electrical contacts. The pair of electrical contacts of each electrical connector 1210, 1211, 1212 may be continuously electrically connected with each other inside of housing 1202, such that the pair of electrical contacts represents a single connection point to a circuit. In such a configuration, it is only necessary that one of the electrical contacts within a pair be connected. Electrical connectors 1210, 1211, and 1212 may include redundant electrical contacts. The electrical contacts of each electrical connector 1210, 1211, 1212 may also represent opposite ends of a circuit, for example, the positive and negative ends of a battery charging circuit.

Returning to FIG. 3, external unit 120 may communicate with implant unit 110. For example, in some embodiments, a primary signal may be generated on primary antenna 150, using processor 144, signal source 142, and amplifier 146. More specifically, in one embodiment, power source 140 may provide power to one or both of the processor 144 and the signal source 142. Processor 144 may cause signal source 142 to generate a signal (e.g., an RF energy signal). Signal source 142 may output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), and a desired magnitude of electric field to be generated by implant electrodes 158a, 158b, etc. Amplifier 146 may output the amplified signal to primary antenna 150.

In some embodiments, external unit 120 may communicate (e.g., transmit) a primary signal from primary antenna 150 to secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. The coupling between the primary and secondary antennas may include capacitive coupling, inductive coupling, radio frequency coupling and any combinations thereof.

Coupling between primary antenna 150 and secondary antenna 152 may depend on the proximity of the primary antenna relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and the secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of the primary signal on primary antenna 150 may cause or induce a secondary signal on secondary antenna 152, the coupling between the two antennas may also lead to a coupled signal or signal components on the primary antenna 150, as a result of the secondary signal present on secondary antenna 152. A signal on primary antenna 150 induced by a secondary signal on secondary antenna 152 may be referred to as a primary-coupled-signal. The primary signal may refer to any and all signals or signal components present on primary antenna 150, regardless of source, and the primary-coupled-signal may refer to any signal or signal component arising on the primary antenna as a result of coupling with signals present on secondary antenna 152. Thus, in some embodiments, the primary-coupled-signal may contribute to the primary signal on primary antenna 150.

Implant unit 110 may respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b. In other embodiments, the response of implant unit 110 may include powering an implanted lamp.

Figure 6:
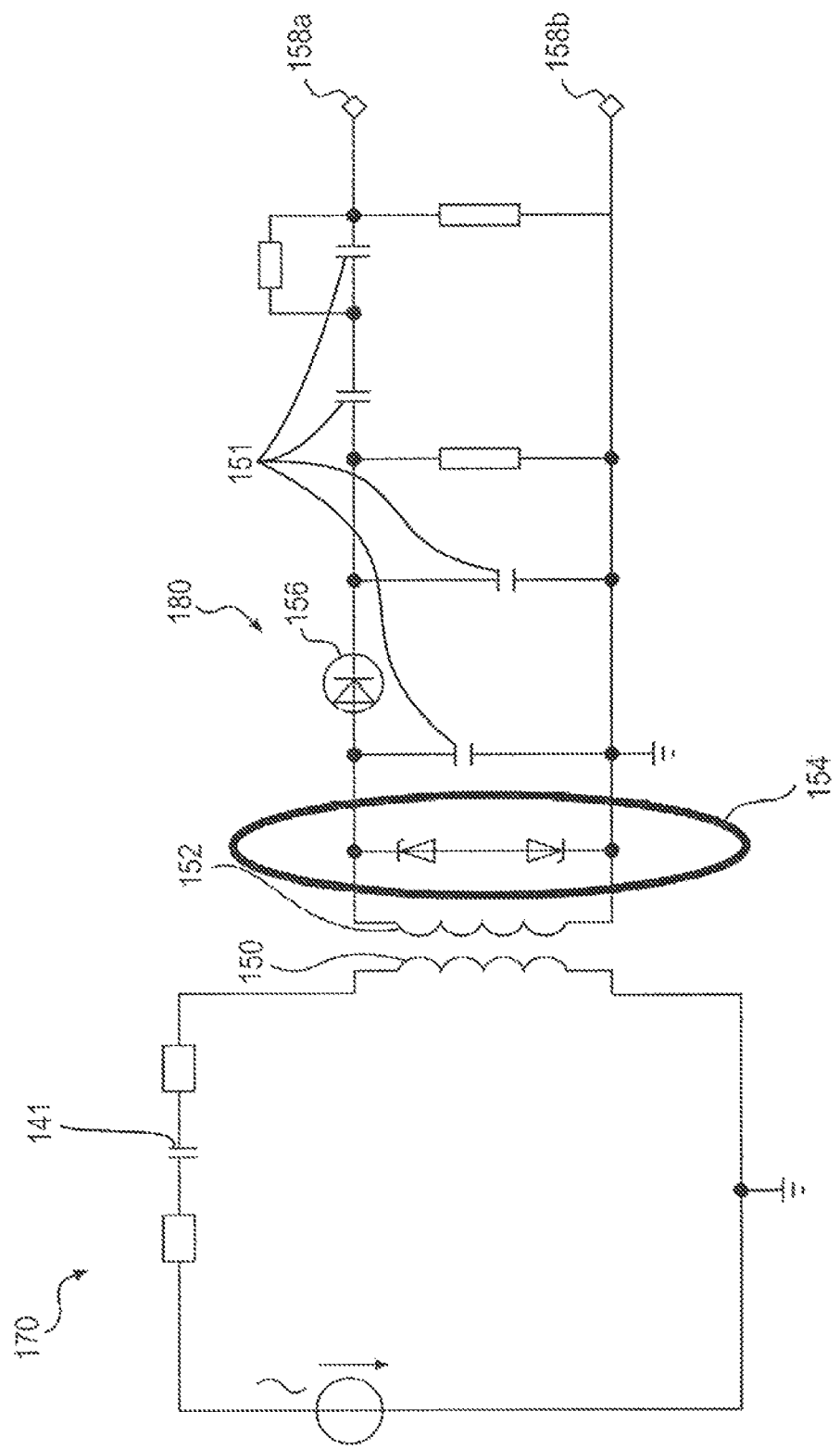
FIG. 6 is circuit diagram of an implant unit and an external unit, according to an exemplary embodiment of the present disclosure.

FIG. 6 illustrates a circuit (170) that may be included in external unit 120 and a circuit (180) that may be included in implant unit 110. Additional, different, or fewer circuit components may be included in either or both of circuitry 170 and circuitry 180. As shown in FIG. 6, secondary antenna 152 may have an electric connection to implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The efficiency of energy transfer between primary antenna 150 and secondary antenna 152 may depend on factors including, for example, how closely a resonant frequency associated with primary antenna 150 (and its associated circuitry 170) matches a resonant frequency associated with secondary antenna 152 (and its associated circuitry 180). Resonant frequencies include frequencies at which electrical circuitry naturally oscillates. In some circumstances, the resonant frequency of the implant unit (e.g., including antenna 152) may match or be substantially equal to the resonant frequency of the external unit (e.g., including primary antenna 150). These circumstances may be referred to as those that provide a resonant frequency match between the implant unit and the external unit. In other circumstances, the resonant frequency of the implant unit may differ from the resonant frequency of the external unit. These circumstances may be referred to as those that provide a resonant frequency mismatch between the implant unit and the external unit.

The degree of frequency matching, for example, between the implant unit and the external unit may be characterized by the proximity of the two resonant frequencies to one another. For example, a resonant frequency match may be considered to occur when a difference between the two resonant frequencies are no more than 30%, 20%, 10%, 5%, 3%, 1%, 0.5%, 0.1%, or less of, for example, the resonant frequency of the external unit. Accordingly, a resonant frequency mismatch, also referred to as simply "frequency mismatch," may be considered to occur when two resonant frequencies do not match. For example, a resonant frequency mismatch may be considered to occur when a difference between two resonant frequencies (e.g., the resonant frequencies of the implant unit and the external unit) are greater than about 30%, 40%, 50%, 60%, or more with respect to one of the resonant frequencies (e.g., the resonant frequency of the external unit). In other embodiments, a resonant frequency match may be deemed to occur when a difference between the two resonant frequencies are no more than about 0.5% of one of the frequencies. The proximity of the two resonant frequencies may affect the energy transfer between the two antennas. For example, the efficiency of energy transfer between two antennas may depend on several factors, one of which may be the degree to which the resonant frequencies of the antennas match. Thus, if all other factors are held constant, changing the resonant frequency of one antenna with respect to the other will alter the efficiency of energy transfer. A resonant frequency match between two antennas may be considered to occur when the efficiency of energy transfer is at least 50%. In some embodiments, a resonant frequency match may be associated with energy transfer efficiencies of 60%, 70%, 80%, 90%, 95% or greater.

The present disclosure includes approaches to change or otherwise control a level of resonant frequency match or mismatch between the external unit and the implant unit. For example, when an implant unit is placed in the body, the change in environment (e.g., because of moisture in the body, etc.) may cause a shift in resonant frequency of the implant unit (including, for example, the implantable circuitry and the secondary antenna of the implant unit). This shift may result in a mismatch between the resonant frequency of the implant unit and the external unit, especially where the resonant frequency of the implant unit and the resonant frequency of the external unit matched prior to implanting the implant unit in the body. Thus, one approach to addressing the frequency mismatch that may result between the implant unit and the external unit may include anticipating the amount of drift resulting from implantation of the implant unit in the body. For example, if the amount of drift is known, can be estimated, calculated, measure, etc., circuitry in the implant unit may be manufactured, adjusted, tuned, etc. prior to implantation in order to account for the expected drift.

In some cases, the drifting of the internal resonant frequency may last for several days to several months after implantation before stabilizing. For example, the resonant frequency of the implant unit may drift from 8.1 kHz to 7.9 kHz. In some embodiments it may be possible to predict by how much the resonant frequency may drift using experimentation or simulation. Thus, in the example above, if a long-term resonant frequency value of 7.9 kHz is desired, the implant unit may be manufactured with a resonant frequency value of 8.1 kHz prior to implantation.

According to some embodiments the internal resonant frequency (e.g., the resonant frequency associated with the implantable circuit and the secondary antenna) may depend on a capacitance associated with the implantable circuit. Therefore, in order to set a specific resonant frequency in some embodiments, the capacitance of the implantable circuit of the implant unit may be adjusted through the addition and/or adjustment of one or more trimming capacitors prior to encapsulation. The amount of adjustment may depend on an expected amount of resonant frequency drift after the implant unit is placed in the body.

Knowing the expected resonant frequency drift, the resonant frequency of the implant unit may be set, for example, by adjusting a capacitance associated with the implantable circuit. In one embodiment, a capacitor associated with the implantable circuit may be adjusted (e.g, laser trimmed) to an particular capacitance value before insertion into implant circuitry. In another embodiment, a capacitor of known value may be inserted into implant circuitry. In still another embodiment, a plurality of capacitors may be inserted into the implanted circuitry to set the capacitance of the implantable circuit and to adjust the resonant frequency of the implant unit. Such a plurality of capacitors may include a series of capacitors each having at least one capacitance value that may be the same or different. The resonant frequency may be calculated based on a particular capacitance value. Alternatively, the resonant frequency value may be iteratively determined after capacitance adjustments. For example, after an adjustment in capacitance, a resulting resonant frequency may be measured. If the resonant frequency has a desired value, then no further adjustments may be necessary. Otherwise, the process of adjusting and measuring may continue iteratively until a desired or target resonant frequency is obtained.

In some embodiments, as discussed above, the capacitance associated with the implantable circuit may be determined such that after the implant unit is placed in the body and after an expected level of resonant frequency drift, the internal resonant frequency of the implantable circuit and the external resonant frequency of the external circuit may be in resonant frequency match. The expected level of drift may be determined through calculations. Alternatively or additionally, the expected level of drift may be determined through testing.

Some embodiments may include methods for manufacturing an implant unit. For example, an implantable circuit may be arranged on a carrier, and an antenna may be arranged on the carrier. The antenna may include an antenna configured to wirelessly receive energy from an external unit and to transfer at least a portion of the received to the implantable circuit. The method may also include determining an expected level of resonant frequency drift for the implant unit and adjusting a capacitance associated with the implantable circuit such that the implant unit, including the secondary antenna and the implantable circuitry, includes a target resonant frequency. A difference between the target resonant frequency and the resonant frequency of the external unit (e.g., including the primary antenna and associated circuitry) may be close to, substantially equal to, or equal to the amount of expected resonant frequency drift experienced by the implant unit after implantation into the body.

In some circumstances, the resonant frequency of the external unit may change during use. For example, when primary antenna 152 is bent to conform to the skin of the subject, the spatial relationship coils within primary antenna 152 may shift, causing a change in resonant frequency. Additionally, contact with moisture or other agents present on the skin may cause a shift in the resonant frequency. Accordingly, another approach to reduce the resonant frequency mismatch between the implant unit and the external unit may focus on adjusting the resonant frequency associated with the external unit. For example, the processor associated with the external unit may be configured to determine a current resonant frequency mismatch between the primary antenna and the secondary antenna associated with the implant unit. In response, the processor may provide an adjustment to at least one component of the circuitry of the external unit to cause a change in the resonant frequency of the external unit. For example, in some embodiments, the processor may apply a plurality of different capacitances to circuitry of the external unit, which may correspond to a plurality of different resonant frequencies for the circuitry. For at least some of the different resonant frequencies, the processor may determine a plurality of energy transmission efficiency values between the external unit and the implant unit. Based on the determined energy efficiency values, the processor may select a particular capacitance value that provides an efficiency above a predetermined threshold or one that is closest to a target efficiency, etc.

In some embodiments, the processor may determine a resonant frequency mismatch based on transmission of a primary signal from the primary antenna to the secondary antenna. The determination may be based on a primary-coupled-signal and the coupling between the primary antenna and the secondary antenna. By monitoring the primary-coupled-signal, the processor may determine the transmission efficiency, which may in turn be an indication of resonant frequency mismatch.

The processor may be configured to determine the level of resonant frequency mismatch based on any suitable conditions. For example, when the processor determines energy transfer efficiency has fallen below a certain threshold (e.g., 70%), the amount of mismatch may be determined, and circuitry associated with the external unit may be adjusted to reduce or eliminate the mismatch. Alternatively or additionally, the processor may periodically monitor a current level of resonant frequency mismatch (e.g., every few seconds, minutes, hours, days, etc.) In some embodiments the processor may monitor a current level of the resonant frequency mismatch at unequal time intervals. For example, the processor may be configured to monitor a level of resonant frequency mismatch between the implant unit and the external unit at shorter time intervals (e.g., every few seconds or minutes) after the implant unit has been newly implanted (e.g., during the first week or month after implantation). As the implant ages, drift in resonant frequency of the implant unit may stabilize. Therefore, as the implant ages, the processor may monitor resonant frequency mismatch more infrequently.

Upon determining a resonant frequency mismatch between the implant unit and the external unit, the processor may adjust the resonant frequency of circuitry in the external unit (e.g., self-resonant transmitter circuit including the primary antenna) to reduce the mismatch. A self-resonant transmitter circuit may include features to permit adjustment of a resonant frequency of the circuit. Such adjustment may take place through the selective inclusion and exclusion of at least one capacitor into or out of a self-resonant transmitter circuit. Adding (or subtracting) capacitors to the self-resonant transmitter circuit may cause a change in the resonant frequency of the circuit. In some embodiments the change in the resonant frequency associated with the primary antenna may cause the resonant frequency of the primary antenna and the resonant frequency of the secondary antenna to substantially match.

In one embodiment, the external unit includes at least one capacitor configured to be selectively included and selectively excluded from the circuit. The processor may adjust the resonant frequency of the primary antenna by selectively including and excluding the at least one capacitor from the circuit. For example, the external unit's circuit may be provided with one or more capacitors or trim capacitors configured, through processor-controlled switches, for selective inclusion and exclusion. The switches may include, for example, transistors or relays. Thus, the processor may include or exclude a capacitor from the circuit by opening or closing a switch associated with the respective capacitor.

A single capacitor associated with a switch or a processor-selectable capacitance value may enable the processor to select between at least two different values of the resonant frequency. In one embodiment, the external unit may include a bank of a plurality of capacitors (e.g., 4, 6, 12, or more), enabling the processor to select a capacitance based on combinations of capacitors. A bank of six capacitors, for example, would yield 64 different capacitance combinations and, in theory, a similar number of resonant frequency values. In some embodiments, the processor may be configured to use more or less than all of the available capacitors for adjusting the circuitry or for testing for resonant frequency mismatch, etc. In some embodiments, capacitors included in a plurality of capacitors available to the processor may each include the same capacitance value or may include various different values.

The at least one processor may selectively include or exclude capacitance values from one or more trimmable capacitors or from one or more of a plurality of capacitors in order to determine a current level of frequency mismatch between the implant unit and external unit. Based on the current level of mismatch, the processor may then attempt to reduce, minimize, or eliminate the current level of mismatch by selectively including or excluding capacitance values from one or more trimmable capacitors or from one or more of a plurality of capacitors in order to set the resonant frequency of the external unit at or near to a desired resonant frequency value. In this way, the processor may attempt to reduce, minimize, or eliminate any mismatch determined to exist between the external unit and the implant unit.

According to one embodiment, the processor may select a combination of capacitors from the plurality of capacitors, to provide a resonant frequency match that surpasses a predetermined threshold. For example, selection of the capacitance values may result in a difference between the resonant frequency of the implant unit and the resonant frequency of the external unit being no more than 10% of the resonant frequency of the external unit.

In some embodiments the processor of the external unit may apply an adjustment to at least one component of the circuit to cause a change in the resonant frequency of the external unit. In an exemplary embodiment, the adjustment includes switching capacitors from a capacitor bank into and out of the circuit. For example, during transmission of a primary signal, the processor may determine a capacitor combination that changes (e.g., increases) transmission efficiency and resonant frequency match. The adjustment may cause a difference in the resonant frequency of the primary antenna and the resonant frequency of the secondary antenna to be no more than 30% of the resonant frequency of the primary antenna, for example. Additionally, the adjustment may enable at least 50% energy transfer efficiency between the external unit and the implant unit.

FIG. 11 depicts an additional embodiment illustrating a self-resonant transmitter circuit employing a modified class D amplifier for use with resonant frequency matching methods. Modified class D amplifier 1600 may be used in place of, or in addition to, any or all of the elements of external unit 120 depicted in FIG. 3. For example, modified class D amplifier 1600 may replace signal source 142 and amplifier 146. In this embodiment, processor 144 may adjust the operation of a class D amplifier to provide a frequency match between a generated signal and a resonant frequency of a primary antenna 150. Because the resonant frequency of primary antenna 150 may be adjusted to match that of secondary antenna 152 during operation, it may be beneficial to adjust the frequency of the generated signal as well to improve efficiency within the self-resonant transmitter circuit of an external unit 120. Modified class D amplifier 1600 may be used to provide such an adjustment as follows. Modified class D amplifier 1600 includes an H bridge 1601 including switches (such as MOSFETs) 1620. Between the switches is self-resonant transmitter circuit 1610. Power to the modified class D amplifier is supplied by supply voltage 1650, which may be supplied from a battery, for example. As shown in FIG. 16, self-resonant transmitter circuit 1610 may include multiple capacitances 1640 and inductances 1660. Capacitances 1640 may include multiple capacitors, combinations of which may be chosen from among capacitors as described above, in order to selectively provide an appropriate value of capacitance 1640. The value of capacitance 1640 may be selected for resonant frequency matching to secondary antenna 152. Inductances 1660 may be provided at least partially by primary antenna 150. Processor 144 may also adjust a driving frequency of the H bridge switches 1620 in order to generate a signal of a frequency that matches the resonant frequency of self-resonant circuit 1610. By selectively opening and closing switches 1620 appropriately, the DC signal of supply voltage 1650 may be converted into a square wave of a selected frequency. This frequency may be selected to match the resonant frequency of self-resonant circuit 1610 in order to increase the efficiency of the circuit.

Figure 12:
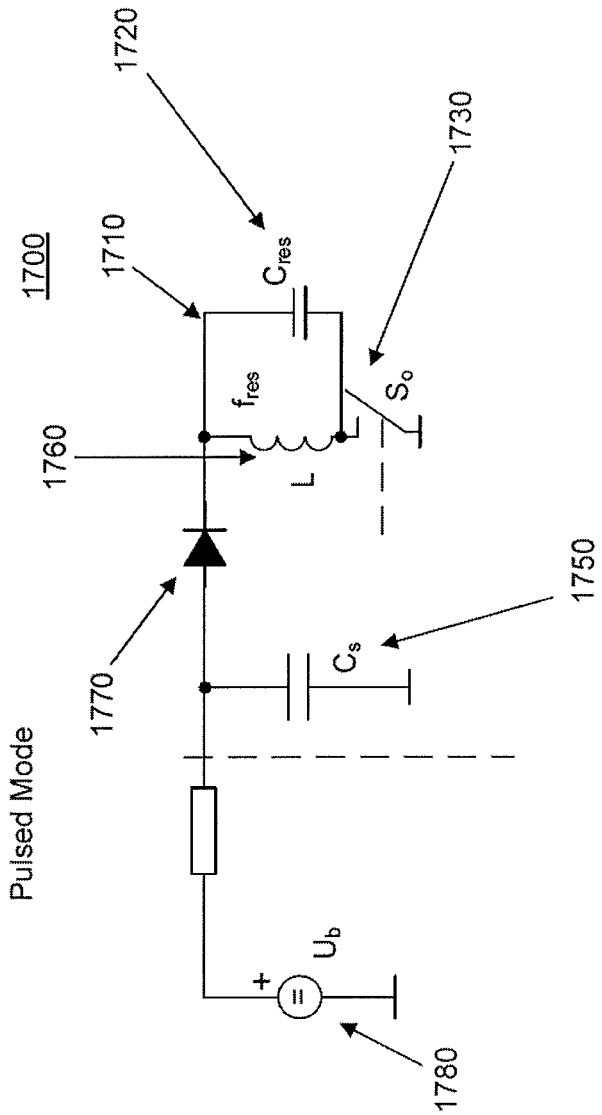
FIG. 12 is circuit diagram depicting a pulsed mode self-resonant transmitter.

FIG. 12 depicts an additional embodiment illustrating a pulsed mode self-resonant transmitter 1700 for use with resonant frequency matching methods. Pulsed mode self-resonant transmitter 1700 may be used in place of, or in addition to, any or all of the elements of external unit 120 depicted in FIG. 3. For example, pulsed mode self-resonant transmitter 1700 may replace signal source 142 and amplifier 146. In this embodiment, processor 144 may control the circuit through a power switching unit, depicted in the present embodiment as switch 1730. A power switching unit may include a transistor, relay, or similar switching device. Pulsed mode self-resonant transmitter 1700 includes a primary power source 1780, for example, a battery or alternative source of power. Transmitter 1700 may include a power storage unit, such as storage capacitor 1750. Other suitable power storage units may also be utilized, such as an inductor and/or battery, as well as combinations of these storage elements. Transmitter 1700 may also include a self-resonant transmitter circuit 1710, including resonance capacitance 1720 and a resonance inductance 1760. Resonance inductance 1760 may be provided at least partially by primary antenna 150.

Transmitter 1700 may operate in the following manner, among others. Processor 144 may control the operation of switch 1730. When switch 1730 is maintained in an open position, current from power source 1780 flows into storage capacitor 1750 which thereby accumulates an electrical charge. When switch 1730 is closed, charged storage capacitor 1750 drives current into the self-resonant circuit 1710 during a current loading period, where energy is stored in inductance 1760. Due to the operation of diode 1770, current flow into circuit 1710 will be cut off after a period of energy accumulation. The current transferred to circuit 1710 will then oscillate freely within circuit 1710 at the resonant frequency of circuit 1710 and thus generate a signal for transmission to the implant through primary antenna 150 (which is included in the circuit and creates at least a portion of inductance 1760). Because the signal is generated by the self-resonance of circuit 1710, it will match the resonant frequency of circuit 1710 and a more efficient transmission may be created.

Components of transmitter 1700 may be chosen such that the current loading period is approximately two microseconds and a period of free oscillation in circuit 1710 is between 10 and 20 microseconds. Other components may be selected, however, to provide any desired current loading period or free oscillation period. As described elsewhere in this disclosure, stimulation pulses of varying lengths may be desired. Stimulation pulses of longer than a single period of free oscillation may be constructed by multiple cycles of loading and releasing energy from storage capacitor 1750 into circuit 1710. Storage capacitor 1750 may itself be chosen to store enough charge to drive a large number of oscillation cycles (e.g., between 10 and 100) in order to construct entire stimulation pulses without requiring recharging from power source 1780.

Pulsed mode self-resonant transmitter 1700 may provide several advantages. As described above, because the transmission signal is generated by the self-resonance of circuit 1710, it likely will match the resonant frequency of circuit 1710, obviating a need to match the frequency of the generated signal with the circuit resonance frequency. Further, because energy is stored in capacitor 1750 prior to discharge into circuit 1710, a greater flexibility in choice of power source 1780 may be provided. Effective neural stimulation may depend on current levels that rise rapidly. To achieve this with a battery alone may require a high-voltage and/or high-current battery. This need may be obviated by transmitter 1700, which permits the delivery of a very high peak current through the use of a relatively low voltage/low current battery. Transmitter 1700 uses fewer switches (e.g., transistors) than does a conventional amplifying circuit. Each switch may be a source of energy loss, contributing to an overall less efficient circuit. The presence of a single switch 1730 in transmitter 1700 may increase the efficiency of the circuit as a whole.

The field inducing signal may be generated as a result of conditioning of the secondary signal by circuitry 180. As shown in FIG. 6, circuitry 170 of external unit 120 may generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158*a* and 158*b*.

As noted above, the field inducing signal may generate an electric field between implant electrodes 158*a* and 158*b*. In some instances, the magnitude and/or duration of the generated electric field resulting from the field inducing signal may be sufficient to modulate one or more nerves in the vicinity of electrodes 158*a* and 158*b*. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158*a*, 158*b* may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158*a* and 158*b*).

Processor 144 may limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also cause application of sub-modulation control signals to primary antenna 150. Such sub-modulation control signals may include an amplitude and/or duration that result in a sub-modulation signal at electrodes 158*a*, 158*b*. While such sub-modulation control signals may not result in nerve modulation, such sub-modulation control signals may enable feedback-based control of the nerve modulation system. That is, in some embodiments, processor 144 may cause application of a sub-modulation control signal to primary antenna 150. This signal may induce a secondary signal on secondary antenna 152, which, in turn, induces a primary-coupled-signal on primary antenna 150.

To analyze the primary-coupled-signal induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary-coupled-signal on primary antenna 150.

The primary-coupled-signal may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary-coupled-signal indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may generate a modulation control signal based on a signal from a user, for example, or a detected level of neural activity in a sensory neuron (e.g., the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In embodiments for the treatment of hypertension, processor 144 may generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

Processor 144 may determine a degree of coupling between primary antenna 150 and secondary antenna 152 by monitoring one or more aspects of the primary-coupled-signal received through feedback circuit 148. In some embodiments, processor 144 may determine a degree of coupling between primary antenna 150 and secondary antenna 152 by monitoring a voltage level associated with the primary-coupled-signal, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary-coupled-signal. This baseline voltage level, for example, may be associated with a range of movement of the patient's tongue when a sleep apnea event or its precursor is not occurring, e.g., during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary-coupled-signal on primary antenna 150 may also change. Processor 144 may recognize a sleep apnea event or its precursor when a voltage level, current level, or other electrical characteristic associated with the primary-coupled-signal changes by a predetermined amount or reaches a predetermined absolute value.

Figure 7:
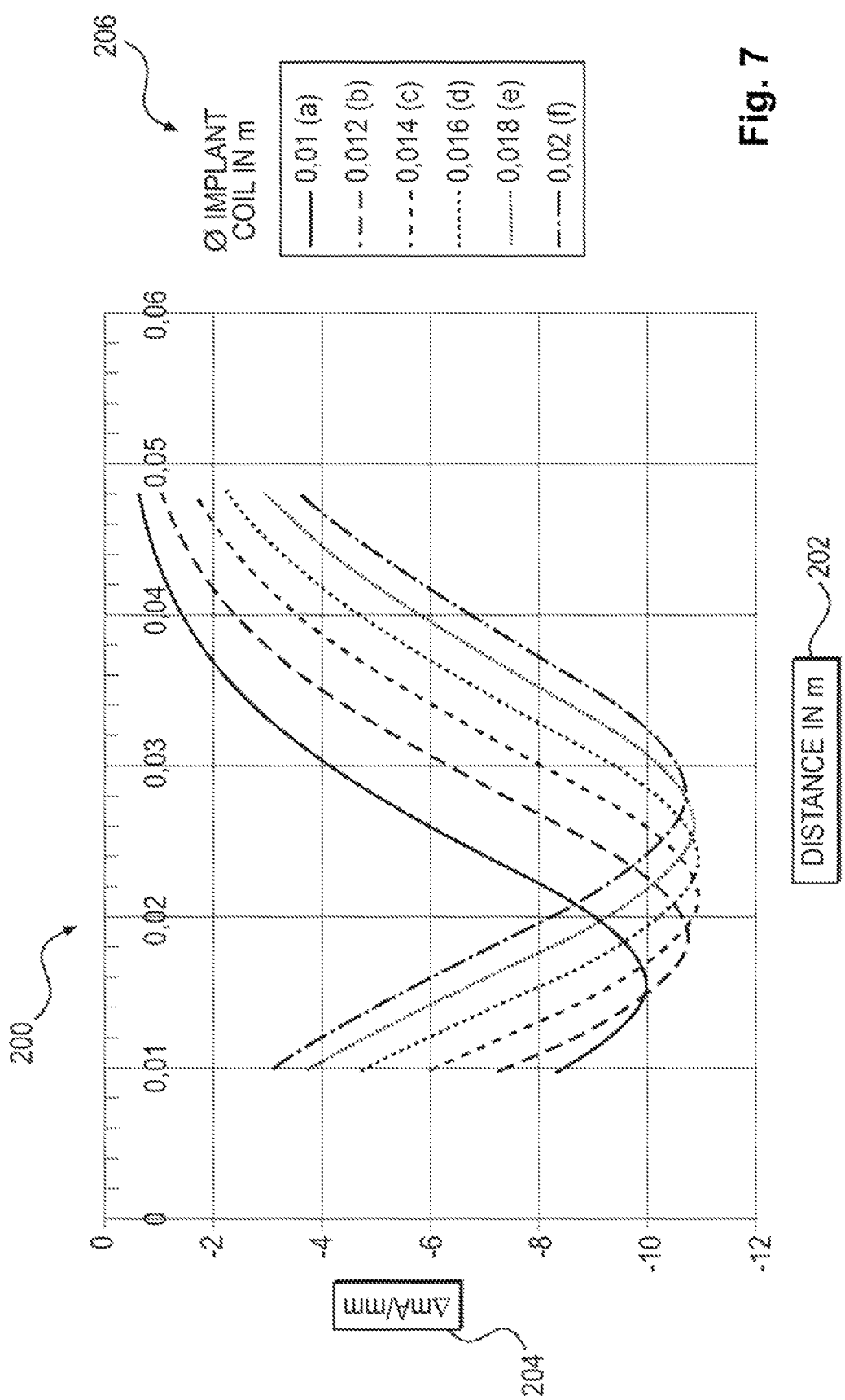
FIG. 7 is a graph illustrating non-linear harmonics, according to an exemplary disclosed embodiment.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary-coupled-signal on primary antenna 150.

Processor 144 may determine a degree of coupling between primary antenna 150 and secondary antenna 152 by monitoring other aspects of the primary-coupled-signal. For example, in some embodiments, the non-linear behavior of circuitry 180 in implant unit 110 may be monitored to determine a degree of coupling. For example, the presence, absence, magnitude, reduction and/or onset of harmonic components in the primary-coupled-signal on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate at multiple frequencies. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary-coupled-signal present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode.

Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
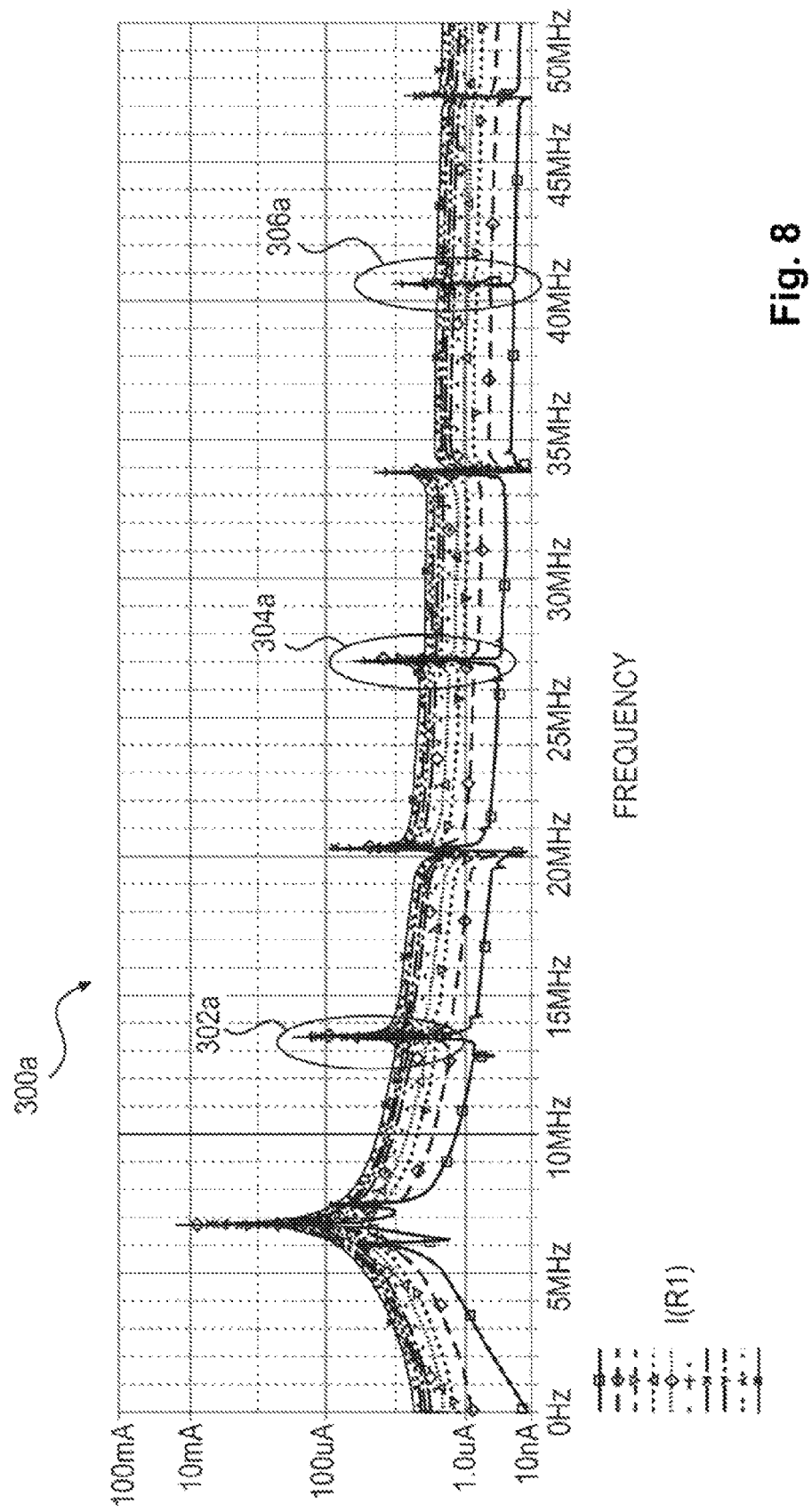
FIG. 8 is a graph of quantities that may be used in determining energy delivery as a function coupling, according to an exemplary disclosed embodiment.
Figure 9:
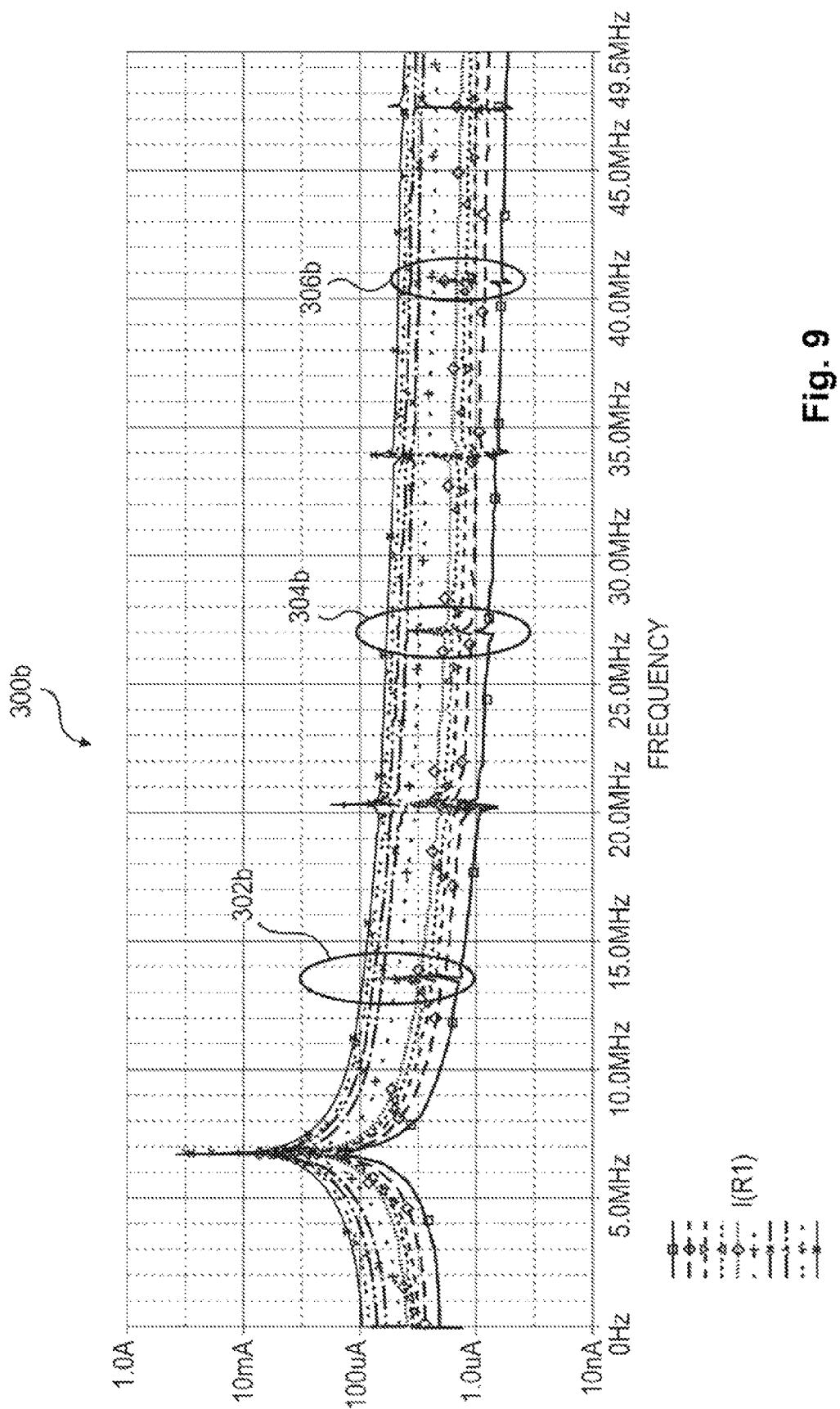
FIG. 9 is a graph of quantities that may be used in determining energy delivery as a function coupling, according to another exemplary disclosed embodiment.

FIGS. 8 and 9 illustrate this effect. For example, FIG. 8 illustrates a graph 300a that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302a), four times the excitation frequency (peak 304a) and six times the excitation frequency (peak 306a). As the amplitude of the excitation signal rises between 10 nanoamps and 40 microamps, the amplitude of peaks 302a, 304a, and 306a all increase.

FIG. 9 illustrates the effect on the even harmonic response of circuitry 180 caused by harmonics modifier circuit 154. FIG. 9 illustrates a graph 300b that shows the oscillatory behavior of circuitry 180 at several amplitudes ranging from about 30 microamps to about 100 microamps. As in FIG. 8 and FIG. 9 shows a primary excitation frequency at about 6.7 MHz and second, fourth, and sixth order harmonics (peaks 302b, 304b, and 306b, respectively) appearing at even multiples of the excitation frequency. As the amplitude of the excitation signal rises, however, between about 30 microamps to about 100 microamps, the amplitudes of peaks 302b, 304b, and 306b do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary-coupled-signal on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These Figures illustrate data based around a 6.7 MHz excitation frequency. These principles, however, are not limited to the 6.7 MHz excitation frequency illustrated, and may be used with a primary signal of any suitable frequency.

In some embodiments, the determined amplitude of the primary signal corresponding to the transition level of the Zener diodes (which may be referred to as a primary signal transition amplitude) may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling) between primary antenna 150 and secondary antenna 152. In other embodiments, processor 144 may calculate a degree of coupling based on performance characteristics of known circuit components.

By periodically determining a degree of coupling value, processor 144 may determine, in situ, appropriate parameter values for the modulation control signal that will ultimately result in nerve modulation. For example, by determining the degree of coupling between primary antenna 150 and secondary antenna 152, processor 144 may select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g., during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g, if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g, movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g, whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may receive a control signal prompting the implant controller to turn on and cause a modulation signal to be applied to the implant electrodes for modulating a nerve. Such a processor may also monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Other embodiments of the present disclosure will be apparent to those skilled in the art from consideration of the specification and practice of the present disclosure.

Additional aspects of the invention are described in the following numbered paragraphs, which are part of the description of exemplary embodiments of the invention. Each numbered paragraph stands on its own as a separate embodiment of the invention.

The invention claimed is:

1. A device for treating sleep apnea from a location external to a body of a subject by wirelessly powering an implant in the body of the subject, and wherein the implant includes a secondary antenna for wirelessly receiving energy, the device comprising:
a housing configured to be located external to the body of the subject at a location between a neck and chin of the subject, the housing including therein:
a primary antenna configured to transmit a modulation signal to the secondary antenna, wherein the modulation signal causes stimulation of a nerve of the subject to treat sleep apnea;
a circuit electrically connected to the primary antenna; and
at least one processor electrically connected to the primary antenna and the circuit, the at least one processor configured to:
determine a resonant frequency mismatch between a first resonant frequency associated with the primary antenna and the circuit and a second resonant frequency associated with the secondary antenna associated with the implant, when the implant is implanted in the body of the subject; and
apply an adjustment to at least one component of the circuit to cause a change in the first resonant frequency associated with the primary antenna and the circuit and a reduction in the resonant frequency mismatch, wherein the adjustment is automatically determined by the at least one processor based on feedback from the secondary antenna associated with the implant.

2. The device of claim 1, wherein the change in the first resonant frequency associated with the primary antenna and the circuit causes the first resonant frequency and the second resonant frequency to substantially match.

3. The device of claim 1, wherein the at least one processor is further configured to determine the resonant frequency mismatch after the implant unit is implanted.

4. The device of claim 1, wherein the adjustment applied to the at least one component causes a difference between the first resonant frequency and the second resonant frequency to be no more than 30% of the first resonant frequency.

5. The device of claim 1, wherein the adjustment applied to the at least one component enables at least 50% energy transfer efficiency between the device and the implant unit.

6. The device of claim 1, wherein the at least one processor is further configured to determine the resonant frequency mismatch by varying the first resonant frequency and determining a transmission efficiency at a plurality of different resonant frequencies.

7. The device of claim 1, wherein the at least one component of the circuit includes at least one capacitor configured to be selectively included and selectively excluded from the circuit, and wherein the at least one processor is further configured to adjust the first resonant frequency by selectively including and excluding the at least one capacitor from the circuit.

8. The device of claim 7, wherein the circuit includes at least one switch associated with respective ones of the at least one capacitor, and wherein the at least one processor is further configured to selectively include and exclude the at least one capacitor from the circuit by opening and closing the at least one switch.

9. The device of claim 7, wherein the at least one capacitor includes a plurality of capacitors enabling a plurality of potential resonant frequency values for the first resonant frequency, and wherein the at least one processor is configured to select a value for the first resonant frequency from among the plurality of potential resonant frequency values and selectively include or exclude capacitors from to circuit capacitors from among the plurality of capacitors to set the first resonant frequency to the selected value.

10. The device of claim 1, wherein the at least one component of the circuit includes a plurality of capacitors each offering at least one capacitance value.

11. The device of claim 10, wherein the at least one processor is further configured to apply the adjustment by selecting for inclusion in the circuit a combination of capacitors from among the plurality of capacitors.

12. The device of claim 10, wherein the at least one processor is further configured to select for inclusion in the circuit a combination of capacitors from the plurality of capacitors to provide a first resonant frequency that provides an energy transfer efficiency above a predetermined threshold.

13. The device of claim 1, wherein the at least one processor is further configured to periodically determine a current level of the resonant frequency mismatch between the primary antenna and the secondary antenna.

14. The device of claim 13, wherein the at least one processor is further configured to determine the current level of resonant frequency mismatch after an energy transfer efficiency between the device and the implant unit falls below a predetermined threshold.

15. The device of claim 1, wherein the at least one processor is further configured to receive the feedback from the secondary antenna associated with the implant at the primary antenna in response to the modulation signal transmitted by the primary antenna.

16. The device of claim 1, wherein the at least one processor is further configured to receive the feedback from the secondary antenna associated with the implant at the primary antenna in response to a sub-modulation signal transmitted by the primary antenna.

17. The device of claim 1, wherein the at least one processor is configured to cause transmission of the modulation signal by the primary antenna based on feedback from the secondary antenna that is indicative of a degree of coupling between the primary antenna and the secondary antenna.

18. The device of claim 1, wherein the housing is configured to be affixed to the body of the subject at the location between the neck and chin of the subject during stimulation of the nerve of the subject to treat sleep apnea.

19. The device of claim 18, wherein the housing further includes therein a power source electrically connected to the at least one processor.

* * * * *

UNITED STATES PATENT AND TRADEMARK OFFICE
CERTIFICATE OF CORRECTION

PATENT NO. : 9,526,906 B2
APPLICATION NO. : 13/952063
DATED : December 27, 2016
INVENTOR(S) : Adi Mashiach Page 1 of 1

It is certified that error appears in the above-identified patent and that said Letters Patent is hereby corrected as shown below:

In the Claims

Claim 3, Column 31, Line 41, delete "unit".

Claim 5, Column 31, Line 49, delete "unit".

Claim 9, Column 32, Line 12, "to circuit capacitors from among the plurality of capacitors" should read --the circuit, from among the plurality of capacitors,--.

Claim 14, Column 32, Line 35, delete "unit".

Signed and Sealed this
Twenty-fifth Day of April, 2017

Michelle K. Lee
*Director of the United States Patent and Trademark Office*